United States Patent [19]

Leenders et al.

[11] Patent Number: 4,670,400
[45] Date of Patent: Jun. 2, 1987

[54] DETERMINATION OF MONOMER CONVERSION BY HEADSPACE ANALYSIS

[75] Inventors: Hendrikus W. Leenders, Arnhem; Derk A. Bril, Giesbeek, both of Netherlands

[73] Assignee: The B. F. Goodrich Company, Akron, Ohio

[21] Appl. No.: 264,919

[22] Filed: May 18, 1981

[51] Int. Cl.$^4$ ............... G01N 31/00; G01N 33/44
[52] U.S. Cl. ............................... 436/34; 436/85; 436/161; 436/181
[58] Field of Search ............... 526/338; 436/34, 85, 436/161, 154, 181

[56] References Cited

U.S. PATENT DOCUMENTS

| | | | |
|---|---|---|---|
| 3,321,280 | 5/1967 | Trotter, Jr. et al. | 436/85 X |
| 3,477,819 | 11/1969 | Fernald et al. | 436/34 |
| 3,746,509 | 7/1973 | Koskan | 436/85 X |
| 3,846,073 | 11/1974 | Baum et al. | 436/85 X |

OTHER PUBLICATIONS

Shapras et al., Analytical Chemistry, vol. 34, No. 3, Mar. 1962, p. 433.

*Primary Examiner*—Arnold Turk
*Attorney, Agent, or Firm*—George A. Kap; Alan A. Csontos

[57] ABSTRACT

Method for determining monomer conversion in the liquid phase by analyzing vapor phase above a polymerization mixture comprising measuring temperature of the vapor phase, analyzing the vapor phase with a gas chromatograph provided with a flame ionization detector to determine relative amount of a certain monomer in the vapor phase, correlating initial amount of the monomer with an intermediate amount of the monomer adjusted by applying a temperature correction, and determining monomer conversion on the basis of an essentially linear relationship of conversion in the liquid phase with relative amount of the monomer in the vapor phase.

15 Claims, No Drawings

DETERMINATION OF MONOMER CONVERSION BY HEADSPACE ANALYSIS

BACKGROUND OF THE INVENTION

Throughout the history of polymerization reactions, the lack of a simple and reliable method for determining the degree of conversion at any time during the reaction has been a serious obstacle in both production control and research study of the polymerizations. A number of techniques, other than total solids conversion, have been proposed for determining degree of monomer conversion but with limited success. For instance, in certain gaseous monomer systems, it is possible to follow reaction pressure to determine degree of monomer conversion, however, this approach is useful in the final stages of polymerization since pressure remains constant until the separate monomer phase is consumed at the end. Dilatometric measurements of the volume changes during polymerization offer a possibility of a highly precise conversion determination but it would be difficult to apply in laboratory and production reactors at similar pressures and agitation conditions. Approximate reaction rate data can also be obtained by measuring cooling water temperatures and flow rates and thus estimate the rate of heat evolution. Refinements of equipment and instrumentation are, however, needed to enhance the accuracy of this method which further would require accurate integration to provide conversion data.

Certain peculiarities relating to polymerization reactions accentuate the need for a better method for determining degree of monomer conversions than is presently available. For instance, low conversion polyvinyl chloride resins, that are blown down at or before the point of pressure drop in the reaction, have become an important factor. In the face of variable monomer purity and other causes of variable reaction rates, pressure and time of polymerization are not a reliable criterion for obtaining consistent final conversions. Certain polymer products require additions of materials or changes in operating conditions at particular conversions, and in research work, studies of polymerization mechanisms are completely dependent on accurate conversion measurements throughout the course of the polymerization.

The most common method for measuring monomer conversion in large-scale production is the solids method. To determine percent monomer conversion, a sample is extracted from the reactor with a flexible vial of known volume. This is accomplished by attaching the vial to a line, evacuating the vial by squeezing it, drawing the liquid sample by releasing the vial so that it expands and fills with the liquid, and closing the valve on the vial. Next, the vial with the liquid sample is weighed, the sample is deposited in a pre-weighed aluminum pan containing hydroquinone short stop solution, the vial is re-weighed to obtain sample weight by difference and the pan with the sample is placed in a drying oven to evaporate all volatiles, i.e., monomers, water, etc. The pan is re-weighed to determine the weight of solids on the basis of which, percent conversion is calculated. In actual plant practice containing dozens of reactors, it is apparent that determination of the sclids conversion is not a simple matter. During the course of polymerization that can take up to one full day, only a few samples are taken. This can lead to many quality variations especially if it is desired to make an addition of a material or make an operating change at a certain solids conversion, since an accurate solids conversion is not available and cannot be pinpointed. Likewise, delay in analysis, which is inherently present in a plant operation due to the time that is required to take and deliver samples to a laboratory, allows the reaction in the vial to continue unabated with the result that inaccurate data is obtained.

The use of gas chromatography to gauge monomer conversion is also known. This technique, introduced by H. Kahn in 1958 for the study of Ziegler - type diene polymerizations, involves periodic chromatographic analysis of vapor samples to determine the decrease in monomer concentration relative to that of a volatile, inert solvent. The invention disclosed herein pertains to improvements in such a method.

SUMMARY OF THE INVENTION

Monomer conversion in the liquid phase is obtained by analyzing the vapor in the headspace of a reactor containing a polymerization mixture, determining relative initial amount of a monomer in the vapor phase by means of a gas chromatograph having a suitable detector, such as flame ionization detector, measuring the temperature of the vapor phase, correlating initial amount of the monomer with an intermediate amount thereof adjusted for temperature deviation from the temperature of the liquid phase, and determining monomer conversion in the liquid phase on the basis of an essentially linear relationship of the conversion in the liquid phase with the relative amount of the monomer in the vapor phase.

DETAILED DESCRIPTION OF THE INVENTION

The method for determining monomer conversion involves the use of a gas chromatograph, or another suitable means, for quantitative analysis of the ratio of the components in gas samples taken at suitable time intervals from the vapor space above the polymerization mixture. The ratio of components in the vapor phase is then correlated with amount of polymer formed. In the case of preparing homopolymers where a single monomer is polymerized, a reference compound is introduced into the polymerization mixture to enable conversion determination. The reference compound has a substantially constant vapor pressure throughout the polymerization reaction relative to the monomer that is polymerized, which makes possible the necessary calibration.

Principal requirements for a reference compound is that it should have a vapor pressure similar to that of the monomer that is polymerized, it should be completely inert in the polymerization, it should not be consumed nor affect polymerization in any chemical or physical way, and it should be rapidly and completely separated from the monomer in the chromatograph column. For polymerization of vinyl chloride, all of the requirements for a reference compound are met by n-butane. Since it is desirable to use a minimum amount of the reference compound to avoid any effect on the polymerization, the monomer concentration is chosen that is sufficient to give an accurately measurable peak on the chromatogram. For vinyl chloride homopolymerization, it was empirically determined that one part by weight of n-butane per 100 parts vinyl chloride has been found satisfactory, and even lower levels might suffice. A number of comparison experiments have demonstrated that n-butane at this concentration has no detectable effect on polymerization rate, molecular weight of polyvinyl chloride, particle size, or polymer properties.

Other reference compounds that can be used in connection with homopolymerization of vinyl chloride include halogenated methane and ethane, such as methyl chloride and ethyl chloride as well as freons, i.e., chlorofluoroalkanes, such as dichlorodifluoroethane.

In a multi-monomer system, it is possible to use one of the monomers to caliberation the rate of conversion in the liquid phase by analysis of the vapor phase. In such a system, the calibrating monomer has such an overwhelmingly greater vapor pressure than the other monomers, that it remains essentially constant through most of the reaction. An example of such a system is butadiene-acrylonitrile where vapor pressure of butadiene is 1081 mm and that acrylonitrile, 39 mm, at 5° C. Corrections for determining conversion by vapor analysis are introduced into butadiene-acrylonitrile systems containing relatively large amounts of acrylonitrile, such as 40% and above. The manner of making such corrections is described herein. In a multi-monomer system where one of the monomers cannot be used as a calibrating monomer due to the fact that vapor pressures of the monomers do not differ sufficiently, a reference compound can be used, as in the homopolymerization reaction described above.

One of the most practical instruments for use in vapor analysis is a gas chromatograph. In the operation of this instrument, an accurate volume of a sample is injected into a chromatograph column and following its analysis, a monomer and reference peaks are recorded indicating relative volume of the materials. A flame ionization detector can be used in conjunction with a gas chromatograph to facilitate analysis. This simplifies analysis since the flame ionization detector gives signals only for organic compounds. Other detectors, such as thermal conductivity detectors, can be used.

Validity of the vapor analysis method has been demonstrated on a large number of polymerizations, and a system was designed and installed for automatically sampling a plurality of reactors located at some distance from the instrument, timing of sampling and other functions, analyzing the samples, and recording results. In addition to the basic chromatograph and recorder, the automatic system includes a gas sampling rack, such as a 6-way slide valve, where samples from reactors are received and sequentially admitted to the chromatograph for analysis; a stream selector controller that determines the sequence of sampling; and a data system, i.e., a computer, for integrating the area under the peaks and then correlating this data via a mathematical formula to provide a percent conversion readout on the recorder. The readout can be used by the operator to make additions of materials to the reactor, as a timing indication to implement a method procedure, or an indication of the degree of polymerization.

It is known that relative monomer depletion in the headspace as a function of conversion is an essentially linear relationship in situations of two or more monomers where vapor pressure of one monomer is much greater than the other monomer(s) in the polymerization reaction. Such a situation exists in the case of butadiene, that has a vapor pressure of 1081 mm at 5° C., and acrylonitrile, that has a vapor pressure of 39 mm at 5° C. It is estimated that during the course of the greater part of polymerization, about 98% of the vapor pressure is that of butadiene and only about 2% is acrylonitrile. In view of this disparity in vapor pressures for butadiene and acrylonitrile, mol fraction of butadiene in the liquid phase as a function of conversion will hardly affect mol fraction of butadiene in the vapor phase. For this reason, it is possible to monitor mol fraction of acrylonitrile depletion in the liquid phase as a function of conversion by monitoring mol fraction of acrylonitrile in the vapor phase, using the following expression:

$$\% \text{ acrylonitrile in vapor phase} = \frac{F_{vcn}}{F_{bd} + F_{vcn}} \times 100 \qquad \text{(Equation I)}$$

where
$F_{vcn}$ = the peak area of acrylonitrile, and
$F_{bd}$ = the peak area of butadiene.

The advantage of this approach is that the analysis becomes independent of nitrogen content in the reactor headspace. Only temperature correction of acrylonitrile in the headspace is necessary due to the relative enrichment of acrylonitrile versus butadiene at higher temperatures.

Initial experimental work conducted in this area gave erratic results with respect to correlating vapor space analysis with conversion in the liquid phase. These results were obtained by conducting the vapor space analysis, making an adjustment for temperature by taking the temperature of the liquid phase, and correlating them with percent conversions obtained by the manual solids conversion method. Unfortunately, this experimental work was based on the erroneous assumption that temperature in the headspace was the same as the temperature in the liquid phase. This problem was overcome by installing a temperature probe in the headspace of the reactor to measure temperature of the vapors. It was thus discovered in a particular reactor, that the temperature difference between the vapor phase and the liquid phase was about 7° C., the vapor phase being cooler than the liquid phase by about 7° C. for polymerizations conducted at about 5° C. The temperature difference will, of course, vary from reactor to reactor depending on the cooling medium, reactor design and capacity, agitation means, temperature of the polymerization reaction, etc.

Another precaution was taken to ensure efficient operation and reliability of results. A level controller was installed in the headspace of the reactor extending below the level of the temperature probe and the sampling tube. In the past, reactors were filled to overcapacity by mistake with the result that the sampling tube, and the equipment connected therewith, was fouled since the liquid phase rose too high and some of it was drawn into the sampling apparatus. The provision of a level controller is especially desirable where reactors are charged automatically since there is no visual observation to detect any mistake.

Generally speaking, equilibrium after loading is established in one-half to one hour after charging a reactor. Furthermore, it was empirically determined that headspace conversion is drastically distorted by addition of a material or making a change while the polymerization reaction is in progress. It also takes about one-half to one hour to establish equilibrium whenever the course of polymerization is disturbed in some manner. Therefore, headspace analysis should not be conducted during or one-half to one hour after a disturbance.

As already mentioned, due to its predominant proportion in the feed and to its relatively high vapor pressure, vapor pressure of butadiene in a butadiene/a- crylonitrile system remains essentially constant until the latter part of the reaction. Towards the end, vapor pressure of butadiene starts falling at some point between 60% and 80% conversion.

The method disclosed herein is valid for conversions where the partial pressure of butadiene is constant throughout most of the reaction. Should it be desired to continue polymerization beyond the point where partial pressure of butadiene drops-off, a correction is made. The correction, is, of course, necessitated by the fact that butadiene is used as a reference compound in the butadiene/acrylonitrile system. Since the reference compound can no longer provide a reference point, a correction is introduced to take care of this discrepancy. The correction involves freezing or holding parameter Fbd in Equation I constant at the last value where partial pressure of butadiene was still unchanged. Parameter Fbd is the peak area of butadiene and represents relative amount of butadiene in the vapor phase. Making such a correction does not cause any problems in plant operation since it is well known at what conversions the reactor pressure starts to decline. If the partial pressure of butadiene declines at 60% conversion,'then the value Fbd at 60% conversion is held constant for conversions beyond 60%. This is true for butadiene/acrylonitrile formulations containing in excess of about 40% acrylonitrile.

It has been observed that, for some reason, reactor pressure starts declining at lower conversions for polymers that contain relatively more acrylonitrile and less butadiene. The reason for this might simply be the relative proportion of butadiene as opposed to acrylonitrile. When amount of butadiene in the reactor is large relative to acrylonitrile, then it would be expected that partial pressure would start dropping at a higher conversion than for a situation where relatively less butadiene were present.

In the experiments described hereinbelow, where polymerization of acrylonitrile and butadiene is exemplified, a reactor with a capacity of about three and a quarter thousand gallons was used. It was initially evacuated and a charge of acrylonitrile and emulsifier was introduced with agitation, along with molecular weight modifier. Temperature was set at 5° C. At this point, butadiene was charged followed by initiators. The temperature of the liquid phase was controlled at about 5° C. during the polymerization reaction with the aid of a cooling jacket circulating ammonia as a cooling fluid. The reaction generally takes place in about one-half to a full day. The polymerization reaction of butadiene and acrylonitrile is well known and there is no need to describe it in any greater detail. Reaction products are polymers of acrylonitrile and butadiene containing up to about 50% acrylonitrile.

The reactor referred to above was additionally fitted with a temperature probe in the headspace, a stainless steel sampling tube, and a level controller. The sampling tube extended from the reactor to the flame ionization detector gas chromatograph for conveyance of vapor samples from the reactor headspace. Since pressure in the reactor initially is high and then declines towards the end of polymerization, no difficulty was experienced in drawing off samples of the vapors. Stainless steel tubing was used to transport the sample to the column, and in order to avoid condensation in the line, a pressure reducer was installed to reduce pressure in the line to about 10 psig. Any other means can be used to prevent condensation which, if not provided, can lead to erroneous results since condensation of the more volatile material in the line will deplete the sample and give abnormal results. The vapor sample was conducted to a gas chromatograph located about 40 meters away from the reactor. The analysis was carried out using a ⅛" O.D. ×2.5 meter stainless steel tubing packed with a Tenax column packing. The column was operated at 120° C. using nitrogen as the carrier gas at flow rate of 15 cc per minute. Care was taken to maintain uniformity of sample size. A particular precaution was observed in achieving high precision with the chromatograph was that of conditioning the column after it had been idle overnight or longer. Even with an automatic sampling system, the first 3 to 6 samples give slightly erratic peaks which can introduce uncertainty in the early conversion figures. While the reason for this behavior is not clear, the error can be minimized by injecting several gas samples in rapid succession before starting to measure peak heights for use in calculating conversions. The recorder provides peak areas from which conversion can be calculated.

The data, below, indicates actual vapor temperature, percent acrylonitrile (VCN) measured by the gas chromatograph, percent headspace conversion (HSC) and percent total solids conversion. Headspace conversion was calculated by an expression that is based on the correlation of vapor phase and liquid phase analysis of actual experiments. The expression is as follows:

$$HSC = \left[ a - \left( b - \frac{(t \times b \times 1.86)}{100} \right) \right] / f \quad \text{(Equation II)}$$

where
a = initial % acrylonitrile in vapor phase
b = intermediate % acrylonitrile in vapor phase
t = temperature of vapors in °C.
f = conversion factor Headspace conversion, or percent monomer conversion in the liquid phase, is defined by the above formula as being the initial percent of acrylonitrile in the vapor phase reduced by the intermediate percent acrylonitrile adjusted by the quantity of temperature in the vapor phase multiplied by the intermediate percent acrylonitrile in the vapor phase at any particular time further multiplied by a temperature factor 1.86, this quantity being divided by 100 and the adjusted initial acrylonitrile being divided by a conversion factor f. The factor f is dependent on relative concentration and type of reactants, type of reactor, reaction temperature, etc. Based on earlier experiments, the following information is presented for use in the above formula:

| Polymer | a | f |
|---------|-------|---------|
| A | 1.530 | 0.00871 |
| B | 1.235 | 0.00913 |
| C | 1.150 | 0.00988 |

Polymers A, B and C are polymers of butadiene and acrylonitrile containing 41%, 33%, and 33% acrylonitrile, respectively. It should be understood that values a and f in the above equation, must be made available beforehand to calculate percent monomer conversion by vapor phase analysis. This is done by polymerizing a specific polymer and obtaining percent acrylonitrile in the vapor phase by Equation I, which will provide values for parameters a and b in Equation II. Headspace conversion is then correlated with total solids conversion, a value for which is obtained by analyzing the liquid phase by the total solids conversion method. With values for a, b and HSC, the factor f can easily be calculated for the particular polymer. Same procedure is used to obtain factor f for other polymers. It should be understood that parameter a, i.e., initial percent of acrylonitrile in the vapor phase, need not be provided beforehand. It can be measured at beginning of a polymerization reactor in the same manner as parameter b. For ease of operation, however, it is provided beforehand to save time since it is a constant value for a particular polymer, assuming identical charging procedure and other process variables.

The parameter a is provided beforehand for another reason. After charging a reactor, some time interval is required to establish equilibrium. Since this time interval was found to be about one-half to one hour, it is difficult to determine this value by gas chromatograph analysis.

TABLE II (1042)

Data for one run is presented below for Polymer B containing 33% acrylonitrile that was polymerized at an unknown pressure but is believed to have been between 2 and 3 atmospheres:

| Time, Hr. | °C., Vapor | % VCN | % HSC | % TSC |
|---|---|---|---|---|
| 0 | 0.0 | 1.2350 | 0 | 0 |
| ½ | 0.0 | 1.2372 | −0.24 | x |
| 1 | 0.0 | 1.2349 | 0.01 | x |
| ½ | 0.0 | 1.2249 | 1.10 | x |
| 2 | 0.0 | 1.2232 | 1.29 | x |
| ½ | 0.0 | 1.1831 | 5.68 | x |
| 3 | 0.0 | 1.1795 | 6.07 | x |
| ½ | 0.0 | 1.1293 | 11.57 | x |
| 4 | 0.0 | 1.0858 | 16.34 | x |
| ½ | 0.0 | 1.0458 | 20.72 | x |
| 5 | 0.0 | 1.0172 | 23.85 | x |
| ½ | 0.0 | 0.9739 | 28.59 | x |
| 6 | 0.0 | 0.8517 | 41.98 | x |
| ½ | 0.0 | 0.7658 | 51.39 | 49.50 |
| 7 | 0.0 | 0.6634 | 62.60 | x |
| ½ | 0.0 | 0.5937 | 70.24 | x |
| 8 | 0.0 | 0.5385 | 76.28 | x |
| ½ | 0.0 | 0.5372 | 76.42 | 73.00 |
| 9 | 0.0 | 0.4969 | 80.84 | x |
| ½ | 0.0 | 0.4635 | 84.50 | x |
| 10 | 0.0 | 0.4223 | 89.01 | x |
| ½ | 0.0 | 0.4002 | 91.43 | 91.40 |

TABLE I (1041)

This data is for three runs of Polymer A containing 41% acrylonitrile that were conducted at 3.0, 2.1, and 2.4 atmospheres, respectively:

| Polymerization Time, hrs. | Run 1 | | | | Run 2 | | | | Run 3 | | | |
|---|---|---|---|---|---|---|---|---|---|---|---|---|
| | °C., Vapor | % VCN | % HSC | % TSC | °C., Vapor | % VCN | % HSC | % TSC | °C., Vapor | % VCN | % HSC | % TSC |
| 0 | 0.0 | 1.5293 | 0 | 0 | .0 | 1.5349 | 0 | 0 | | 1.5349 | 0 | 0 |
| ½ | 1.0 | 1.5240 | 2.75 | x | −2.5 | 1.5051 | −6.24 | x | 0.3 | 1.5024 | 3.01 | x |
| 1 | 2.0 | 1.5486 | 3.20 | x | −2.5 | 1.4153 | 4.75 | x | 0.2 | 1.4626 | 7.32 | x |
| ½ | 0.3 | 1.5379 | −1.11 | x | −2.5 | 1.2819 | 21.03 | x | 0.0 | 1.4299 | 10.52 | x |
| 2 | 0.3 | 1.5290 | −0.08 | x | −2.5 | 1.1834 | 33.07 | x | −0.2 | 1.3995 | 13.48 | x |
| ½ | 0.3 | 1.4748 | 6.21 | x | −2.5 | 1.0746 | 46.36 | x | −0.5 | 1.3581 | 17.48 | x |
| 3 | 0.3 | 1.4249 | 12.01 | x | −2.5 | 0.9959 | 55.97 | x | −0.7 | 1.3175 | 21.71 | x |
| ½ | 0.3 | 1.3999 | 14.92 | x | −2.5 | 0.8752 | 70.72 | x | −0.8 | 1.2642 | 27.75 | x |
| 4 | 0.3 | 1.2809 | 28.75 | x | −1.1 | 0.9613 | 63.05 | x | −1.0 | 1.2161 | 32.94 | x |
| ½ | 0.3 | 1.1784 | 40.65 | x | −1.1 | 0.9531 | 64.03 | 60.00 | −1.1 | 1.1045 | 45.98 | x |
| 5 | 1.7 | 1.1237 | 50.35 | x | −1.1 | 0.9750 | 61.35 | x | −1.1 | 1.0306 | 54.79 | x |
| ½ | 0.3 | 1.0612 | 54.29 | x | −1.1 | 0.9666 | 62.42 | x | −1.1 | 0.9759 | 61.31 | x |
| 6 | 0.3 | 1.0904 | 50.89 | x | −1.1 | 0.9250 | 67.38 | x | −0.0 | 1.0044 | 60.25 | x |
| ½ | 0.3 | 1.0623 | 54.16 | x | −1.1 | 0.8917 | 71.35 | x | −0.4 | 0.9884 | 61.28 | 71.00 |
| 7 | 0.3 | 0.9992 | 61.49 | 70.50 | −2.5 | 0.8669 | 71.73 | x | −0.4 | 0.9514 | 65.64 | x |
| ½ | −0.4 | 0.9556 | 65.14 | x | −1.1 | 0.8575 | 75.42 | 78.00 | −0.4 | 0.9078 | 70.77 | x |
| 8 | −0.4 | 0.9294 | 68.23 | x | −1.1 | 0.8285 | 78.88 | x | −0.4 | 0.8684 | 75.41 | x |
| ½ | −0.4 | 0.9043 | 71.18 | x | −1.1 | 0.7927 | 83.15 | 82.50 | −0.4 | 0.8408 | 78.66 | x |
| 9 | −0.4 | 0.8704 | 75.17 | x | | | | | −0.4 | 0.8318 | 79.72 | x |
| ½ | −0.4 | 0.8112 | 82.08 | x | | | | | −0.4 | 0.7919 | 84.41 | x |
| 10 | −0.4 | 0.7384 | 90.17 | 89.60 | | | | | −0.4 | 0.7586 | 88.33 | 88.50 |
| ½ | | | | | | | | | −0.4 | 0.7045 | 94.70 | 90.30 |

It should be apparent that the correlation between headspace conversion and total solids conversion for acrylonitrile in the liquid phase is commending. Although headspace conversion in Run 1 at 7 hours was 61.49% versus total solids conversion of 70.50%, the values narrowed to 90.17% versus 89.60% after 10 hours of reaction. Intermediate conversion values for Run 2 are much better than in Run 1. For instance, in Run 2 at 5 hours, HSC was 64.03% whereas TSC of 60.00%.

The data above demonstrates an incredibly close correlation between headspace conversion and total solids conversion for Polymer B. For instance, HSC and TSC at 6½ hours were 51.39% and 49.50%, and at 8~ hours they were 76.42% and 73.00%, respectively. The final conversions were 91.43% for HSC and 91.40% for TSC.

TABLE III (1052)
This table presents data for polymerization of Polymer C containing 33% acrylonitrile. The two polymerization reactions were conducted at 3.0 and 2.6 atmospheres, respectively.

| Time, Hrs. | Run 1 | | | | Run 2 | | | |
|---|---|---|---|---|---|---|---|---|
| | °C., Vapor | % VCN | % HSC | % TSC | °C., Vapor | % VCN | % HSC | % TSC |
| 0 | 0.0 | 1.1420 | 0 | 0 | 0.0 | 1.1531 | 0 | 0 |
| ½ | 0.0 | 1.1385 | 1.16 | x | 0.3 | 1.1499 | 0.65 | x |
| 1 | 0.0 | 1.1103 | 4.01 | x | 0.3 | 1.1083 | 4.84 | x |
| 1½ | 0.0 | 1.0644 | 8.66 | x | 0.3 | 1.0671 | 8.99 | x |
| 2 | 0.0 | 1.0242 | 12.73 | x | 0.3 | 1.0064 | 15.10 | x |
| 2½ | 0.0 | 0.9693 | 18.28 | x | 0.3 | 0.9250 | 23.29 | x |
| 3 | 0.0 | 0.9232 | 22.95 | x | 0.3 | 0.8725 | 28.57 | x |
| 3½ | 0.0 | 0.8735 | 27.98 | x | 0.3 | 0.8269 | 33.16 | x |
| 4 | 0.0 | 0.8285 | 32.54 | x | 0.3 | 0.7464 | 41.27 | x |
| 4½ | 0.0 | 0.7851 | 36.93 | x | 0.3 | 0.6819 | 47.76 | x |
| 5 | 0.0 | 0.7046 | 45.08 | x | 0.3 | 0.6190 | 54.09 | x |
| 5½ | 0.0 | 0.6282 | 52.81 | x | 0.3 | 0.5494 | 61.09 | x |
| 6 | 0.0 | 0.5630 | 59.41 | x | 0.3 | 0.4785 | 68.23 | x |
| 6½ | 0.0 | 0.5216 | 63.60 | x | 0.3 | 0.4309 | 73.02 | x |
| 7 | 0.0 | 0.4678 | 69.04 | x | 0.3 | 0.3836 | 77.78 | 62.50 |
| 7½ | 0.0 | 0.4386 | 72.00 | x | 0.3 | 0.3817 | 77.97 | .x |
| 8 | 0.0 | 0.4202 | 73.86 | x | 0.3 | 0.3784 | 78.31 | x |
| 8½ | 0.0 | 0.4052 | 75.38 | x | 0.3 | 0.3967 | 76.46 | x |
| 9 | 0.0 | 0.3817 | 77.76 | x | 0.3 | 0.3700 | 79.15 | x |
| 9½ | 0.0 | 0.3745 | 78.49 | x | 0.3 | 0.3644 | 79.71 | x |
| 10 | 0.0 | 0.3556 | 80.40 | x | 0.3 | 0.3533 | 80.83 | x |
| 10½ | 0.0 | 0.3477 | 81.20 | 76.20 | 0.3 | 0.3470 | 81.47 | 78.00 |
| 11 | 0.0 | 0.3247 | 83.53 | x | 0.3 | 0.3275 | 83.43 | x |
| 11½ | 0 | 0.3205 | 83.95 | x | 0.3 | 0.3112 | 85.17 | 85.25 |
| 12 | | 0.3049 | 84.80 | 82.10 | 0.3 | | | |

Correlation between headspace conversion and total solids conversion in Run 1 is adequate and provides meaningful data for an operator, especially when considered in the context of an actual plant operating many reactions that would otherwise be manually sampled and the delay in obtaining analysis results. Results for headspace conversion and total solids conversion in Run 2 correlate very closely.

We claim:

1. Method for determining monomer conversion in the liquid phase by analysis of the vapor phase above a polymerization mixture containing at least one monomer and a reference compound, said reference compound can be one of the monomers when the mixture contains plural monomers, the method comprising measuring temperature in vapor phase, analyzing the vapors to determine amount of a monomer in the vapor phase relative to the reference compound, adjusting the determination of the amount of the monomer in the vapor phase relative to the temperature in the vapor phase, and calculating monomer conversion utilizing the adjusted amount of the monomer.

2. Method of claim 1 that includes, in determining monomer conversion, the step of reducing initial determination of the amount of the monomer in the vapor phase that is a constant for a particular polymer by the adjusted amount of the monomer in the vapor phase determined during the course of polymerization to obtain monomer conversion.

3. Method of claim 2 including the step of adjusting the reduced initial amount of the monomer by a factor that is a constant for a particular polymer in the determination of monomer conversion.

4. Method of claim 3 wherein initial amount of the monomer is determined after establishing equilibrium and the factor is determined beforehand by obtaining monomer conversion by total solids analysis of the liquid phase for a particular polymerization system.

5. Method of claim 3 wherein the reference compound has a substantially constant vapor pressure during the greater portion of the polymerization reaction and is a calibrating monomer or an inert substance, and wherein determination of the monomer conversion in the liquid phase by analysis of the vapor space is determined on the basis of an essentially linear relationship between monomer conversion in the liquid phase and relative amount of the same monomer in the vapor phase.

6. Method of claim 5 wherein the reference monomer is used in polymerization of more than one monomer, it is itself polymerized, and it has a disproportionately greater vapor pressure than other monomer or monomers in the reaction; whereas the inert substance is used in polymerization of one monomer or monomers whose vapor pressure does not differ sufficiently, it does not enter into the polymerization reaction, and it has a disproportionately lower vapor pressure than the monomer.

7. Method of claim 6 including the steps of conveying the vapors to a gas chromatograph to determine relative amount of a monomer in the vapor phase, and reducing pressure of the vapors being conveyed to the chromatograph to prevent condensation thereof.

8. Method of claim 6 including the steps of conveying the vapors to a gas chromatograph equipped with a flame ionization detector, reducing pressure of the vapors being conveyed to the chromatograph to prevent condensation thereof, and analyzing the vapors for organic compounds while ignoring inorganic compounds and gases.

9. Method of claim 6 wherein vinyl chloride monomer is homopolymerized in presence of n-butane as reference compound in amount of about 1 part by weight or less per 100 parts of the monomer.

10. Method of claim 6 wherein parameter Fbd, which represents amount of the monomer in the vapor phase during polymerization, is held constant at a value corresponding to the point where vapor pressure of the reference compound starts to decline in determining monomer conversion by the following relationship:

$$\% \text{ acrylonitrile in vapor phase} = \frac{Fvcn}{Fbd + Fvcn}$$

where Fvcn and Fbd represent relative amounts of acrylonitrile and butadiene, respectively, in the vapor phase obtained by chromatographic analysis of a vapor sample.

11. Method of claim 10 wherein butadiene and acrylonitrile monomers are polymerized, with butadiene being the reference compound, amount of acrylonitrile in the polymer varying up to about 50%.

12. Method of claim 11 including the step of determining liquid level of the reaction mixture and discontinuing feeding of the reactants to a reaction when a predetermined limit is reached.

13. Method of claim 11 wherein amount of the monomer in the vapor phase during polymerization is frozen at about 60% conversion for polymers containing more than about 40% acrylonitrile.

14. Method of claim 11 wherein monomer conversion in the liquid phase is determined on the basis of an essentially linear relationship between monomer conversion in the liquid phase and relative amount of acrylonitrile in the vapor phase as defined by the following equation:

$$\% \text{ conversion} = \left[ a - \left\{ b - \frac{(t \times b \times 1.86)}{100} \right\} \right] / f$$

where
a = initial % acrylonitrile
b = intermediate % acrylonitrile
t = temperature in headspace in °C.
f = conversion factor the monomer conversion being computed by using predetermined values for a and f that are constant for a particular polymer prepared by a certain procedure and are obtained empirically, and value b being obtained by chromatographically analyzing a vapor sample.

15. Method of claim 14 including the step of conveying vapors to a gas chromatograph equipped with a flame ionization detector, reducing pressure of the vapors to prevent condensation thereof, and analyzing the vapors for organic compounds while ignoring inorganic compounds and gases.

* * * * *